United States Patent [19]
Bullock et al.

[11] 3,979,203
[45] Sept. 7, 1976

[54] SULFONAMIDO HERBICIDAL COMPOSITIONS AND PLANT CONTROL METHODS USING THE SAME

[75] Inventors: Milon Walker Bullock, Hopewell; Bryant Leonidas Walworth, Pennington, both of N.J.

[73] Assignee: American Cyanamid Company, Stamford, Conn.

[22] Filed: Sept. 12, 1974

[21] Appl. No.: 505,407

Related U.S. Application Data

[62] Division of Ser. No. 219,123, Jan. 19, 1972.

[52] U.S. Cl. .................................................. 71/103
[51] Int. Cl.² ............................................ A01N 9/14
[58] Field of Search ...................................... 71/103

[56] References Cited
UNITED STATES PATENTS

| | | | |
|---|---|---|---|
| 3,321,292 | 5/1967 | Soloway et al. | 71/103 |
| 3,367,949 | 2/1968 | Soper | 71/103 |
| 3,672,864 | 6/1972 | Maranetz | 71/103 |

FOREIGN PATENTS OR APPLICATIONS

| | | | |
|---|---|---|---|
| 1,223,619 | 2/1971 | United Kingdom | 71/103 |
| 1,128,217 | 9/1968 | United Kingdom | 71/103 |

*Primary Examiner*—Joseph Paul Brust
*Attorney, Agent, or Firm*—H. G. Jackson

[57] ABSTRACT

The present invention relates to novel substituted-1-phenol-4-sulfonamides and salts thereof. It also relates to a method for controlling undesirable plant species with said compounds, and particularly to a novel method for selectively controlling wild oats with said compounds by contacting the seeds or foliage of said wild oat plants with a herbicidally effective amount thereof.

8 Claims, No Drawings

SULFONAMIDO HERBICIDAL COMPOSITIONS AND PLANT CONTROL METHODS USING THE SAME

This is a division of copending application Ser. No. 219,123, filed Jan. 19, 1972.

The present invention relates to novel compounds and salts of compounds having the formula:

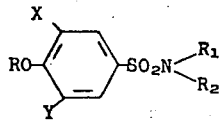

wherein X represents a member selected from the group consisting of H, Br, and Cl; Y represents a member selected from the group consisting of $NO_2$, Br, and Cl; R represents a member selected from the group consisting of H, acyl $C_1$–$C_4$ and N-alkylcarbamoyl $C_1$–$C_4$; $R_1$ represents a member selected from the group consisting of H, alkyl $C_1$–$C_6$ and alkynyl $C_2$–$C_6$; and $R_2$ represents a member selected from the group consisting of alkyl $C_1$–$C_6$ and alkynyl $C_1$–$C_6$, with the proviso that when X is H then Y must be $NO_2$.

This invention also relates to a method for controlling undesirable plant species with compounds having the above formula; and further, it is directed to a method for selectively controlling wild oats in the presence of the cereal grains, especially wheat and barley.

Preferred compositions which are particularly useful as selective preemergence and selective postemergence herbicides effective for controlling wild oats are compounds having the above formula, wherein X and Y each represent members selected from the group Br and Cl; R is H or —CO—NH—$CH_3$; $R_1$ is H or $CH_3$; and $R_2$ is $CH_3$.

In accordance with the invention, the above-identified compounds can be prepared by halogenating the appropriate N-substituted or -N,N-disubstituted-1-phenol-4-sulfonamide. For compounds wherein X and Y both represent the same halogen, the appropriate 1-phenol-4-sulfonamide is generally first dissolved in an inert solvent, such as aqueous acid or base, and then treated with excess halogen. The reaction may be carried out at room temperature, or where desired, the solution of the 1-phenol-4-sulfonamide may be heated before being treated with the halogenating agent. If a mixed halogen product is desired, the appropriate N-substituted or N,N-disubstituted-1-phenol-4-sulfonamide can be dispersed in an organic solvent, such as benzene, treated with a sulfuryl halide, and heated to reflux to obtain the mono-halo-substituted-1-phenol-4-sulfonamide. This product is then dissolved in aqueous base and treated with excess halogen which differs from the halogen of the sulfuryl halide.

The nitrated sulfonamide can be obtained by reacting a N-substituted or N,N-disubstituted-1-phenol-4-sulfonamide with the nitrating agent, preferably nitric acid, dissolved in sulfuric acid. Such reaction yields the corresponding 2-nitro-1-phenol-4-sulfonamide which can then be halogenated in accordance with the procedures given above to yield the 2-nitro-6-halo-1-phenol-4-sulfonamide.

The 1-acyl-2,6-disubstituted-N or -N,N-disubstituted-1-phenol-4-sulfonamides can be obtained by reacting the appropriate phenol sulfonamide with an alkyl anhydride in the presence of base. Similarly, when the appropriate phenol sulfonamide is treated with an alkyl isocyanate, the corresponding carbamoyl compound is obtained. This reaction is generally carried out in the presence of an organic solvent, such as a lower alkyl ketone, at a temperature between about −10°C. and +10°C.

Also in accordance with the present invention, the above-identified compounds can be formulated as dusts, dust concentrates, wettable powders and granular products which can be applied to the habitat of undesirable weeds. In practice, we have found that the active compounds are effective as preemergence as well as postemergence herbicidal agents. They are effective when applied at rates as low as 0.5 pounds per acre and can be used at rates as high as 25 pounds per acre, with a preferred rate of application between about 0.5 and 10 pounds per acre.

Dust formulations are generally prepared by grinding together from about 1% to 25% by weight of the active ingredient and from about 99% to 75% by weight of a solid diluent, such as kaolinite, attapulgite, diatomaceous earth, pumice, talc, or the like. Dust concentrates are similarly prepared excepting that generally about 26% to 95% by weight of the active ingredient is ground together with about 74% to 5% by weight of the solid diluent. Wettable powders are prepared in the same manner as the dust concentrates; however, in addition to the diluent and active ingredient, there is generally also added about 1% to 5% by weight of a dispersing agent, such as sodium lignosulfonate, the sodium salt of a polymeric carboxylic acid or an alkaline earth metal salt of a polymerized alkyl aryl sulfonic acid, and about 1% to 5% by weight of a surface-active agent, such as a polyoxyethylated vegetable oil, naphthalene sulfonic acid condensate, alkyl phenoxy polyoxyethylene ethanol, sodium alkylnaphthalene sulfonate, or the like.

Granular formulations can be prepared by wetting the surface of granular carriers, such as particulate clays (i.e., kaolin, attapulgite, bentonite, etc.), silica, particulate limestone, and ground corn cobs, with a binder solution and coating the wetted particles with a dust or dust concentrate prepared with the active agent. Sugar solutions, liquid fertilizer solutions, and solutions of alkali metal lignosulfonates can all be used as binders in the preparation of these formulations. Granular formulations can also be prepared by dissolving the active agent in an organic solvent, such as acetone, methylene chloride, cyclohexanone, or the like, and spraying the granular particles with the thus-prepared solution.

In order that the present invention may be more fully understood, the following examples are given primarily by way of illustration. No specific details or enumerations contained therein should be construed as limitations on the present invention except insofar as they appear in the appended claims. All parts and percentages are by weight unless otherwise specifically designated.

EXAMPLES 1–3

Preparation of 2,6-Dibromo-N,N-dimethyl-1-phenol-4-sulfonamide

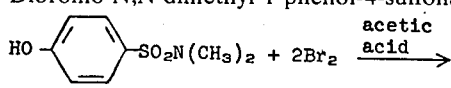

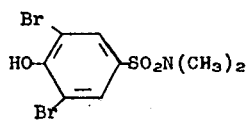

A solution of 2.01 grams (10 millimoles) of N,N-dimethyl-4-hydroxybenzenesulfonamide in 20 ml. acetic acid is treated with a solution of 3.2 grams (20 millimoles) of bromine in 20 ml. acetic acid. The mixture is left standing at room temperature a few minutes and then warmed gently on the steam bath to complete the reaction. The solvent is removed with a rotary evaporator and the residue triturated with water and filtered. The filter cake is washed with water and dried. The yield is 2.7 grams of material melting at 120°C. to 134°C. Recrystallization from acetonitrile gives 1.0 gram of product, melting point 140°C. to 143°C. A second 1.0 gram of material, melting point 123°C. to 130°C. is obtained from the mother liquor by evaporation of the acetonitrile and recrystallization from an ethanol-water mixture. The two crops are combined and dissolved in 20 ml. of warm acetic acid and 3 grams of bromine is added. After standing for two hours, 25 ml. of carbon tetrachloride is added and the solvents evaporated on the steam bath. The reside is recrystallized from 95% ethanol to yield 2.17 grams of product, melting point 160°C. to 161°C.

Analysis calculated for $C_8H_9Br_2NO_3S$: C, 26.80; H, 2.55; Br, 44.50; N, 3.90. Found: C, 27.31, 27.88, 27.50; H, 2.66, 2.79, 2.80; Br, 44.60, 44.33, 42.50; N, 4.10.

The above-identified product is also prepared by the following procedure.

Bromine (27.5 grams, 0.172 mole) is added with stirring to a warm solution of N,N-dimethyl-1-phenol-4-sulfonamide (15.3 grams, 0.076 mole) (Beil. 11, II, 136) in water containing two equivalents of sodium hydroxide. The solution is acidified with hydrochloric acid before extracting with ether. The ether is washed with water until the wash is neutral, dried over magnesium sulfate, and evaporated in vacuo. The resulting crude solid is recrystallized for 95% ethanol-water to give 21.5 grams (78.4%), melting point 158°C. to 160°C. In a similar manner, bromination of the corresponding p-hydroxybenzenesulfonamides gives the following compounds:

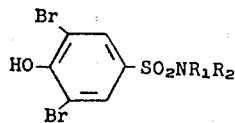

| Example Number | Structure | | Melting Point °C. |
|---|---|---|---|
| | $R_1$ | $R_2$ | |
| 2 | —$C_3H_7$-n | —$C_3H_7$-n | 122.5–124° |
| 3 | H | —$C_2H_5$ | |

EXAMPLE 4

Preparation of 2,6-Dibromo-N-methyl-1-phenol-4-sulfonamide

Bromine (1.7 grams, 0.11 mole) is added with stirring to a warm solution of N-methyl-1-phenol-4-sulfonamide (5.0 grams, 0.027 mole) (Beil. 11, II, 136) in water. The solid obtained, when the reaction solution is chilled in ice, is dissolved in ether and the solution dried over magnesium sulfate. Evaporation in vacuo gives an oil which solidified upon cooling and scratching. Recrystallization from 95% ethanol-water gives 2.4 grams (26.0%) white solid, melting point 202°C. to 204°C.

Analysis Calculated for $C_7H_7Br_2NO_3S$: C, 24.37; H, 2.05; N, 4.06; S, 9.29; Br, 46.33. Found: C, 24.38; H, 2.10; N, 3.92; S, 9.16; Br, 46.42.

EXAMPLES 5–6

Preparation of 2,6-Dichloro-N,N-dimethyl-1-phenol-4-sulfonamide

Excess chlorine is passed into a solution of N,N-dimethyl-1-phenol-4-sulfonamide (5.1 grams, 0.025 mole) in glacial acetic acid. After the addition is complete, the solution is allowed to stand at room temperature. Crude product precipitates which when crystallized from benzene gives 3.1 grams (45.4%) solid, melting point 160°C. to 161.5°C.

Analysis Calculated for $C_8H_9Cl_2NO_3S$: C, 35.56; H, 3.36; N, 5.19; S, 11.87; Cl, 26.25. Found: C, 35.78; H, 3.47; N, 5.60; S, 12.18; Cl, 25.48 and 25.39.

In a similar chlorination of N,N-diethyl-1-phenol-4-sulfonamide gives 2,6-dichloro-N,N-diethyl-1-phenol-4-sulfonamide.

EXAMPLE 7

Preparation of 2,6-Dibromo-N,N-dimethyl-1-phenol-4-sulfonamide, propionate

Propionic anhydride (15.7 grams, 0.12 mole) is reacted with 2,6-dibromo-N,N-dimethyl-1-phenol-4-sulfonamide (6.0 grams, 0.017 mole) in aqueous sodium hydroxide solution. The resulting brown oil was stirred in water overnight to produce a brown solid. Two recrystallizations from 95% ethanol (utilizing a charcoal treatment) gave 3.25 grams of (47.5%) white product, melting point 147°C. to 148°C.

Analysis Calculated for $C_{11}H_{13}Br_2NO_4S$: C, 31.82; H, 3.16; N, 3.37; S, 7.72; Br, 38.50 Found: C, 32.05; H, 3.11; N, 3.41; S, 7.71; Br, 38.50.

EXAMPLE 8

Preparation of 2,6-Dibromo-4-(dimethylsulfamoyl)phenyl carbamic acid, methyl ester Methylisocyanate (5.55 grams, 0.097 mole) is added dropwise to a solution of 2,6-dibromo-N,N-dimethyl-1-phenol-4-sulfonamide (9.35 grams, 0.026 mole) in 40 ml. acetone at 5°C. After stirring for 30 minutes, the acetone is evaporated in vacuo and the product stirred in aqueous 5% sodium carbonate to remove any unreacted sulfonamide. The product is collected by filtration to yield 7.64 grams (70.8%) product, melting point 177°C. to 178.5°C. The analytical sample had melting point 178°C. to 180°C.

Analysis Calculated for $C_{10}H_{12}Br_2N_2O_4S$: C, 28.86; H, 2.91; Br, 38.41; N, 6.73; S, 7.70. Found: C, 29.01; H, 3.24; Br, 38.13; N, 6.67; S, 7.80.

EXAMPLE 9

Preparation of
2-Chloro-N,N-dimethyl-1-phenol-4-sulfonamide

Sulfuryl chloride (18.36 grams, 0.136 mole) is added to a solution of N,N-dimethyl-1-phenol-4-sulfonamide (27.34 grams, 0.136 mole) in 75 ml. benzene at reflux. After refluxing 1 hour, the benzene is evaporated in vacuo to leave 33.0 grams crude material. Recrystallization from benzene gives 21.14 grams (60.4%) product, melting point 102°C. to 104°C.

This compound is the intermediate for the mixed halide of Example 10.

EXAMPLE 10

Preparation of
2-Bromo-6-chloro-N,N-dimethyl-1-phenol-4-sulfonamide

Bromine (3.1 grams, 0.019 mole) dissolved in chloroform is added dropwise to a solution of 2-chloro-N,N-dimethyl-1-phenol-4-sulfonamide (3.5 grams, 0.015 mole) in 10% aqueous sodium hydroxide. The solid resulting from acidifying the reaction solution after first treating it with sodium meta-bisulfite is dissolved in ether. This solution is washed with water until the wash is neutral, dried over magnesium sulfate, and evaporated in vacuo to yield 4.85 grams (71.0%) crude solid, melting point 160°C. to 163°C. This solid is combined with 0.7 grams crude product, melting point 158°C. to 162°C., from a small preliminary run and recrystallized from benzene to give 4.10 grams (75.2% recovery) product, melting point 164.5°C. to 166°C.

Analysis Calculated for $C_8H_9BrClNO_3S$: C, 30.54; H, 2.88; Br, 25.40; Cl, 11.27; N, 4.45; S, 10.19. Found: C, 30.71; H, 2.86; Br, 25.50; Cl, 11.20; N, 4.25; S, 10.32.

EXAMPLE 11

Preparation of
N,N-Dimethyl-2-nitro-1-phenol-4-sulfonamide

Nitric acid (d. 1.42, 3.5 ml., 0.075 mole) dissolved in sulfuric acid is added dropwise with cooling to a solution of N,N-dimethyl-1-phenol-4-sulfonamide (10.0 grams, 0.05 mole), dissolved in 12 ml. sulfuric acid and cooled to 0°C. After all of the nitric acid has been added, the entire reaction is carefully poured onto water-ice, and the yellow solid which results is recrystallized from 95% ethanol to give 7.85 grams (63.8%) product, melting point 116°C. to 118°C.

Analysis Calculated for $C_8H_{10}N_2O_5S$: C, 39.02; H, 4.09; N, 11.38; S, 13.02. Found: C, 39.32; H, 4.07; N, 11.11; S, 13.22.

EXAMPLE 12

Preparation of
2-Bromo-N,N-dimethyl-6-nitro-1-phenol-4-sulfonamide

Bromine (4.2 grams, 0.026 mole) is dissolved in 20 ml. chloroform and added slowly to a well-stirred solution of N,N-dimethyl-2-nitro-1-phenol-4-sulfonamide (5.0 grams, 0.020 mole) in 22 ml. N sodium hydroxide (0.022 mole) and 50 ml. of water. The red-brown solid which formed is removed and dissolved in ether which is washed with water, dried over $MgSO_4$, and evaporated in vacuo. The resulting product is recrystallized from 95% ethanol to give 3.92 grams (60.4%) product, melting point 148°C. to 149°C.

Analysis Calculated for $C_8H_9BrN_2O_5S$: C, 29.55; H, 2.79; Br, 24.58; N, 8.62. Found: C, 29.70; H, 2.78; Br, 24.42; N, 8.68.

EXAMPLES 13–18

Preparation of
2,6Dichloro-N-methyl-1-phenol-4-sulfonamide 3,5-Dichloro-4-hydroxybenzenesulphonyl chloride (5.2 grams, 0.02 mole) [W. L. Hall, *Journal of Organic Chemistry* 31: 2672 (1966)] is partially dissolved in dry benzene (75 ml.). To this mixture under constant stirring, methylamine (approximately 2.48 grams, 0.08 mole) in benzene (75 ml.) is added dropwise. The reaction mixture is allowed to stir for one hour to yield a tarry solid. The benzene is decanted off and the solid stirred in 10% HCl (150 ml.) overnight. The solid is filtered, air-dried, and crystallized from acetate-benzene, hexane (roughly 1:6) to give 2.59 grams (50.5%) with melting point 201°C. to 202°C.

Analysis Calculated for $C_7H_7NO_3SCl_2$: C, 32.83; H, 2.76; N, 5.47; S, 12.52; Cl, 27.69. Found: C, 32.78; H, 2.50; N, 5.46; S, 12.43; Cl, 27.57.

In a similar manner, 3,5-dichloro-4-hydroxybenzenesulphonyl chloride is allowed to react with the appropriate amine to give the following compounds:

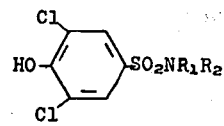

| Example Number | $R_1$ | $R_2$ | Melting Point °C. |
|---|---|---|---|
| 14 | H | $-C_2H_5$ | 183–184° |
| 15 | H | $-C_4H_9$-tert | 243–245° |
| 16 | H | $-C(CH_3)_2C \equiv CH$ | 178–179.5° |
| 17 | H | $-C_3H_7$-i | 131–133° |
| 18 | $-C_4H_9$-i | $-C_4H_9$-i | 120–121.5° |

EXAMPLE 19

The selective postemergence herbicidal activity of the preferred compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures in sufficient quantity to provide the equivalent of about 0.5 to 10 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table I where it can be seen that the preferred compounds are uniquely effective for the control of wild oats. The specificity is demonstrated by the findings that wheat, winter rye, and barley are not injured or only very mildly affected by the preferred compounds at rates which provide effective control of the wild oats.

Plant Abbreviations

AW — Alligator weed
BW — Bindweed
CT — Canada thistle
JC — Johnson grass
NS — Nutsedge
QG — Quackgrass
KO — Kochia
LA — Lambsquarters
MU — Mustard
PI — Pigweed
BA — Barnyard grass
CR — Crabgrass
GRF — Green foxtail
WO — Wild oats
COR — Corn
COT — Cotton
SOY — Soybean
SB — Sugar beets
WH — Wheat
TO — Tomato
RAG — Ragweed
WR — Winter rye
BAR — Barley

| Rating System: | % Difference in Growth from the Check[1] |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |

4 - abnormal growth, i.e., a definite physiological malformation but with an over-all effect less than a 5 on the rating scale.
[1] Based on visual determination of stand, size, vigor, chlorosis, growth malformation and over-all plant appearance.

TABLE I

Selective Postemergence Herbicidal Activity

| Structure | Treatment lb./acre | Perennial Weeds | | | | | | | | Annual Weeds | | | | | |
|---|---|---|---|---|---|---|---|---|---|---|---|---|---|---|---|
| | | AW | BW | CT | JG | NS | QG | KO | LA | MU | PI | BA | CR | GRF | WO |
| HO-(3,5-Br₂)C₆H₂-SO₂N(CH₃)₂ | 10 | 3 | 9 | 0 | 0 | 0 | 3 | 5 | 9 | 3 | 1 | 1 | 1 | 9 | |
| HO-(3,5-Br₂)C₆H₂-SO₂NHCH₃ | 3 | | | | | | | | 7 | 1 | | | | 9 | |
| | 1 | | | | | | | | 6 | 1 | | | | 9 | |
| HO-(3,5-Cl₂)C₆H₂-SO₂N(CH₃)₂ | 10 | | | | | | | 6 | 6 | 3 | 3 | 7 | | 9 | |
| | 2 | 9 | 9 | 0 | 0 | 0 | 1 | 4 | 5 | 9 | 1 | 1 | 0 | 9 | |
| | 1 | | | | | | 0 | 1 | 5 | 1 | 0 | 0 | 0 | 9 | |
| HO-(3-Cl,5-Br)C₆H₂-SO₂N(CH₃)₂ | 10 | 9 | 9 | 0 | 0 | 0 | 6 | 6 | 9 | 4 | 1 | 1 | 1 | 9 | |
| | 2 | 9 | 9 | 0 | 0 | 0 | 6 | 3 | 6 | 6 | 1 | 1 | 1 | 9 | |
| | 1 | | | | | | 1 | 1 | 6 | 5 | 1 | 1 | 0 | 9 | |
| CH₃NHCO-O-(3,5-Br₂)C₆H₂-SO₂N(CH₃)₂ | 10 | 1 | 6 | 0 | 0 | 0 | 0 | 0 | 9 | 9 | 0 | 0 | 0 | 9 | |
| | 1 | | | | | | | | 5 | 1 | | | | 9 | |
| HO-(3-Cl)C₆H₃-SO₂NHCH₃ | 5 | 0 | 1 | 2 | 0 | 0 | 0 | 9 | 9 | 9 | 3 | 2 | 8 | 9 | |
| | 4 | | | | | | | 3 | 5 | 2 | 1 | 1 | 1 | 9 | |
| | 0.5 | | | | | | | 0 | 0 | 0 | 0 | 0 | 0 | 8 | |

TABLE I-continued

Selective Postemergence Herbicidal Activity

| Structure | Treatment lb./acre | COR | COT | SOY | SB | Crops TO | WH | RAG | WR | BAR |
|---|---|---|---|---|---|---|---|---|---|---|
| HO-[3,5-Br₂-C₆H₂]-SO₂N(CH₃)₂ | 10 | | | | | 9 | 0 | | | |
| HO-[3,5-Br₂-C₆H₂]-SO₂NHCH₃ | 3<br>1 | | | | 1<br>1 | | 1<br>0 | | | |
| HO-[3,5-Cl₂-C₆H₂]-SO₂N(CH₃)₂ | 10<br>2<br>1 | 0 | 1 | 3 | 0 | 9 | 0 | | | |
| HO-[3-Cl-5-Br-C₆H₂]-SO₂N(CH₃)₂ | 10<br>2<br>1 | 1 | 1 | 3 | 0 | 9 | 0 | | | |
| CH₃NHCO-[3,5-Br₂-C₆H₂]-SO₂N(CH₃)₂ | 10<br>1 | | | | | 9 | 3<br>0 | | | |
| HO-[3,5-Cl₂-C₆H₂]-SO₂NHCH₃ | 5<br>4<br>0.5 | 2 | 1 | 2 | 0 | | 8<br>1<br>0 | 5 | 2 | |

EXAMPLE 20

The selective preemergence herbicidal activity of the compounds of the invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.50 to 9 pounds per acre of test compound per cup. The treated cups are then placed on greenhouse benches and cared for in accordance with greenhouse procedures. Three weeks after treatment, the tests are terminated and each cup is examined and rated according to the rating system set forth in the preceding example. The tabulated results of these tests establish the herbicidal proficiency of the test compounds for controlling wild oats and several other undesirable plant species without injury to the cereal grains, wheat and barley. Results are reported in Table II.

TABLE II

Selective Preemergence Herbicidal Activity

| Structure | Treatment lb./acre | KO | LA | MU | PI | BA | CR | GRF | WO |
|---|---|---|---|---|---|---|---|---|---|
| 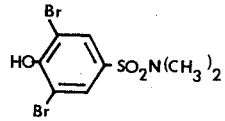 | 9<br>4<br>3 | 9<br><br>9 | 5<br><br>8 | 9<br><br>9 | 9<br><br>6 | 4<br><br>0 | 9<br><br>0 | 9<br><br>4 | 9<br>8<br>9 |
| 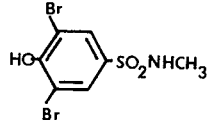 | 6<br>4<br>1.5<br>1 | 9<br><br>0 | 4<br><br>0 | 9<br><br>0 | 9<br>8<br>7 | 3<br><br>0 | 6<br><br>0 | 3<br><br>4 | 8<br><br>9<br>8 |
| 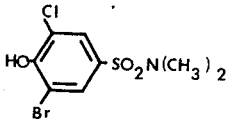 | 9<br>3 | 9<br>9 | 7<br>0 | 9<br>0 | 9<br>9 | 0<br>0 | 7<br>1 | 9<br>5 | 9<br>8 |
| 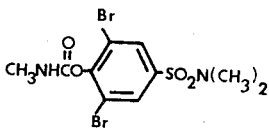 | 9<br>3 | 8<br>8 | 3<br>0 | 9<br>1 | 9<br>9 | 0<br>0 | 1<br>0 | 5<br>0 | 9<br>9 |
| 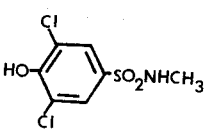 | 9<br>3<br>0.5 | 7<br>5<br>0<br>0 | 7<br>5<br>0<br>0 | 9<br>8<br>3<br>0 | 4<br>4<br>0<br>0 | 8<br>7<br>0<br>0 | 7<br>4<br>0<br>0 | 9<br>9<br>7<br>0 | 9<br>9<br>8 |

| Structure | Treatment lb./acre | COR | COT | SOY | SB | Crops WR | WH | RAG | BAR |
|---|---|---|---|---|---|---|---|---|---|
| 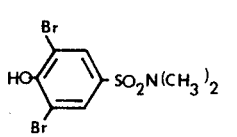 | 9<br>4<br>3 | 0<br>0<br>0 | 0<br><br>0 | 0<br>0<br>0 | 9<br><br>9 | <br>0<br> | <br>0<br> | | |
| 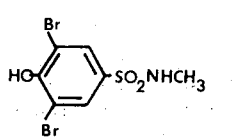 | 6<br>4<br>1.5<br>1 | 1<br>5<br>0<br>0 | 0<br><br>0 | 4<br>0<br>0<br>0 | 4<br><br>0 | <br>0<br><br>0 | | | |
| 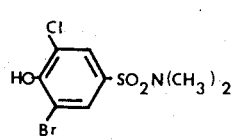 | 9<br>3 | 0<br>0 | 0<br>0 | 1<br>0 | 5<br>1 | | | | |
| 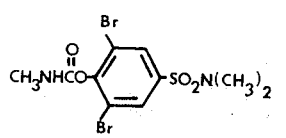 | 9<br>3 | 0<br>0 | 0<br>0 | 7<br>0 | 9<br>3 | | | | |

TABLE II-continued
Selective Preemergence Herbicidal Activity

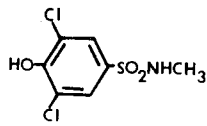

| | | | | | | | |
|---|---|---|---|---|---|---|---|
| 9 | 7 | 4 | 7 | 8 | | 7 | |
| 3 | 1 | 4 | 2 | 4 | | 3 | |
| 0.5 | | | | | 2 | 0 | 1 |
| | 0 | 0 | 0 | 0 | | 0 | |

EXAMPLE 21

The postemergence herbicidal activity of other compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures in sufficient quantity to provide the equivalent of about 2.0 to 10 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provided in a preceding example. The data obtained are reported in Table III.

EXAMPLE 22

The preemergence herbicidal activity of several other compounds of the invention is exemplified by the following tests in which the seeds of a variety of monocotyledonous and dicotyledonous plants are separately mixed with potting soil and planted on top of approximately one inch of potting soil in separate pint cups. After planting, the cups are sprayed with the selected aqueous acetone solution containing test compound in sufficient quantity to provide the equivalent of about 3 to 15 pounds per acre of test compound per cup. The treated cups are then placed on greenhouse benches and cared for in accordance with greenhouse procedures. Three weeks after treatment, the tests are terminated and each cup is examined and rated according to the rating system set forth in a previous example. The tabulated results of these tests establish the herbicidal proficiency of the test compounds and are reported in Table IV below.

TABLE III

| Structure | Treatment lb./acre | Postemergence Herbicidal Activity | | | | | | | | | | | | | Crops |
|---|---|---|---|---|---|---|---|---|---|---|---|---|---|---|---|
| | | Perennial Weeds | | | | | | Annual Weeds | | | | | | | |
| | | AW | BW | CT | JG | NS | QG | KO | LA | MU | PI | BA | CR | GRF | WO | RAG |
| 2,6-Dibromo-1-phenol-N,N-di-n-propyl-4-sulfonamide | 10 | | 6 | 9 | 0 | 0 | 0 | 9 | 6 | 9 | 9 | 1 | 1 | 3 | 1 | |
| | 2 | | 3 | 1 | 0 | 0 | 0 | 9 | 1 | 9 | 9 | 1 | 1 | 1 | 0 | |
| 2,6-Dichloro-N,N-diisobutyl-1-phenol-4-sulfonamide | 9 | | | | | | | | 6 | 9 | 9 | 1 | 1 | 8 | 1 | 5 |
| | 3 | | | | | | | | 5 | 9 | 8 | 1 | 1 | 5 | 1 | 2 |
| 2,6-Dichloro-N-isopropyl-1-phenol-4-sulfonamide | 5 | 1 | 1 | 1 | 0 | 0 | 0 | | 1 | 9 | 1 | 1 | 1 | 1 | 1 | 9 |
| 2-Bromo-N,N-dimethyl-6-nitro-1-phenol-4-sulfonamide | 10 | | 8 | 9 | 0 | 1 | 0 | 1 | 4 | 9 | 6 | 1 | 1 | 0 | 6 | |
| | 2 | | 1 | 6 | 0 | 0 | 0 | 1 | 4 | 3 | 8 | 1 | 1 | 0 | 1 | |
| 2,6-Dichloro-N-ethyl-1-phenol-4-sulfonamide | 10 | 1 | 9 | 9 | 0 | 0 | 0 | 7 | 9 | 9 | 2 | 2 | 8 | 8 | 9 | |
| | 2 | 1 | 9 | 9 | 0 | 0 | 0 | 3 | 9 | 9 | 1 | 1 | 5 | 5 | 3 | |
| N-tert-Butyl-2,6-dichloro-1-phenol-4-sulfonamide | 10 | 1 | 9 | 9 | 1 | 0 | 0 | 5 | 9 | 8 | 1 | 2 | 9 | 1 | 9 | |
| | 2 | 1 | 9 | 9 | 0 | 0 | 0 | 2 | 9 | 7 | 1 | 1 | 5 | 0 | 9 | |

TABLE IV

| Structure | Treatment lb./acre | Preemergence Herbicidal Activity | | | | | | | | Crops | | | |
|---|---|---|---|---|---|---|---|---|---|---|---|---|---|
| | | Annual Weeds | | | | | | | | | | | |
| | | KO | LA | MU | PI | BA | CR | GRF | WO | COR | COT | SOY | SB | RAG |
| 2,6-Dichloro-N-isopropyl-1-phenol-4-sulfonamide | 9 | | 3 | 7 | 9 | 5 | 4 | 9 | 4 | 0 | 1 | 0 | 3 | 3 |
| | 3 | | 0 | 4 | 6 | 4 | 4 | 4 | 0 | 0 | 0 | 0 | 0 | 0 |
| Benzenesulfonamide, N-tert-butyl-3,5-dichloro-4-hydroxy-, compound with tert-butylamine | 9 | | 7 | 8 | 9 | 6 | 8 | 9 | 4 | 4 | 2 | 2 | 7 | 9 |
| | 3 | 2 | 5 | 8 | 4 | 5 | 5 | 4 | 4 | 2 | 0 | 2 | 6 | |
| 2,6-Dibromo-N,N-dimethyl-1-phenol-4-sulfonamide propionate | 15 | 6 | 5 | 1 | 9 | 2 | 7 | 9 | 7 | | | | | |
| | 5 | 0 | 5 | 1 | 8 | 2 | 7 | 8 | 7 | | | | | |
| N,N-Dimethyl-2-nitro-1-phenol-4-sulfonamide | 7.5 | 5 | 1 | 8 | 6 | 9 | 0 | 5 | 4 | | | | | |

TABLE IV-continued

Preemergence Herbicidal Activity

| Structure | Treatment lb./acre | Annual Weeds | | | | | | | | Crops | | | | |
|---|---|---|---|---|---|---|---|---|---|---|---|---|---|---|
| | | KO | LA | MU | PI | BA | CR | GRF | WO | COR | COT | SOY | SB | RAG |
| 2-Bromo-N,N-dimethyl-6-nitro-1-phenol-4-sulfonamide | 15<br>5 | 9<br>9 | 8<br>3 | 9<br>9 | 9<br>5 | 3<br>3 | 5<br>0 | 8<br>0 | 9<br>9 | | | | | |
| 2,6-Dichloro-N-ethyl-1-phenol-4-sulfonamide | 9<br>3 | ·<br> | 7<br>3 | 8<br>6 | 9<br>7 | 4<br>0 | 8<br>3 | 7<br>4 | 8<br>5 | 1<br>0 | 1<br>0 | 7<br>2 | 7<br>2 | 9<br>7 |
| N-tert-Butyl-2,6-dichloro-1-phenol-4-sulfonamide | 9<br>3 | | 8<br>7 | 9<br>7 | 9<br>9 | 6<br>4 | 7<br>3 | 8<br>6 | 4<br>4 | 4<br>4 | 1<br>0 | 3<br>0 | 8<br>2 | 9<br>9 |
| 2,6-Dichloro-N,N-diisobutyl-1-phenol-4-sulfonamide | 9 | | 2 | 2 | 6 | 2 | 2 | 2 | 0 | | | | | 8 |

EXAMPLE 23

The selectivity and specificity of the compounds of the present invention for controlling wild oats in the presence of wheat and barley is demonstrated by the following tests.

In these tests, field plots in North Dakota, with a past history of heavy infestation of wild oats (*Avena fatua*), were planted with hard red spring wheat and barley. The plots were 8 feet by 24 feet and sprayed immediately after planting with an aqueous wettable powder suspension in sufficient amount to provide 3 pounds per acre of the test compound, 2,6-dichloro-N-methyl-1-phenol-4-sulfonamide. Four replicates per treatment were used. Seven weeks after planting and treatment, the plots were examined and rated according to the system used in Example 19. An 80% wettable powder formulation was used and had the following analysis:

| | % W/W |
|---|---|
| 2,6-Dichloro-N-methyl-1-phenol-4-sulfonamide | 80.00 |
| Dioctyl ester of sodium sulfosuccinic acid | 1.25 |
| Sodium lignosulfonate | 4.00 |
| Silica | 9.75 |
| Kaolinite | 5.00 |
| | 100.00 |

Data obtained are reported below.

| | Preemergence Activity | | | | | | | | | | | |
|---|---|---|---|---|---|---|---|---|---|---|---|---|
| | Wild Oats | | | | Wheat | | | | Barley | | | |
| Rate | I | II | III | IV | I | II | III | IV | I | II | III | IV |
| 3 lb./acre | 5 | 7 | 5 | 7 | 0 | 0 | 0 | 0 | 0 | 0 | 0 | 0 |

Postemergence activity was determined at the aboveidentified location using the same plant species and wettable powder formulation. Applications, however, of the test compound were made to the foliage of the growing plants at the two-leaf and the four-leaf stage of the wild oats. Plots were examined and rated about seven weeks after planting. Data obtained are reported below.

| | Postemergence at Two-Leaf Stage of Wild Oats | | | | | | | | | | | |
|---|---|---|---|---|---|---|---|---|---|---|---|---|
| | Wild Oats | | | | Wheat | | | | Barley | | | |
| Rate | I | II | III | IV | I | II | III | IV | I | II | III | IV |
| 1 lb./acre | 8 | 8 | 5 | 7 | 0 | 0 | 0 | 0 | 0 | 0 | 0 | 0 |
| 2 lb./acre | 9 | 8 | 8 | 9 | 0 | 0 | 0 | 0 | 0 | 0 | 0 | 0 |

| | Postemergence at Four-Leaf Stage of Wild Oats | |
|---|---|---|
| Rate | Wild Oats | Wheat |
| 2 lb./acre | 8 | 0 |

We claim:

1. A method for the control of undesirable plant species comprising contacting said undesirable plant species with a herbicidally effective amount of a compound having the formula:

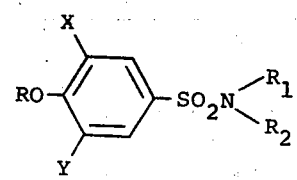

where X is a member selected from the group H, Br, and Cl; Y is a member selected from the group $NO_2$, Br, and Cl; R is a member selected from the group H, alkanoyl $C_1-C_4$ and N-alkylcarbamoyl $C_1-C_4$; $R_1$ is a member selected from the group H, alkyl $C_1-C_6$ and alkynyl $C_2-C_6$; $R_2$ is a member selected from the group alkyl $C_1-C_6$ and alkynyl $C_1-C_6$, with the proviso that when X is H then Y must be $NO_2$.

2. A method for the control of wild oats comprising applying to the habitat of said wild oats a herbicidally effective amount of a compound having the formula:

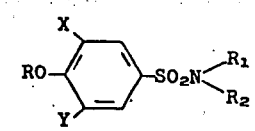

where X and Y are Br or Cl; R is H or —CO—NH—$CH_3$; $R_1$ is H or $CH_3$; and $R_2$ is $CH_3$.

3. A method for the selective control of wild oats in the presence of cereal grains comprising applying to soil containing seeds of said wild oats and cereal grains a herbicidally effective amount of a compound of the formula:

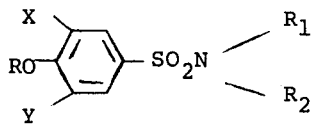

where X and Y are Br or Cl; R is H or —CO—N-H—CH$_3$; R$_1$ is H or CH$_3$; and R$_2$ is CH$_3$.

4. A method for the selective control of wild oats in the presence of cereal grains comprising applying to the foliage of said wild oats a herbicidally effective amount of a compound of the formula:

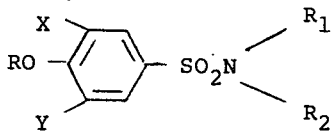

where X and Y are Br or Cl; R is H or —CO—N-H—CH$_3$; R$_1$ is H or CH$_3$; and R$_2$ is CH$_3$.

5. A method according to claim 1 wherein the compound is: 2,6-dibromo-N,N-dimethyl-1-phenol-4-sulfonamide.

6. A method according to claim 1 wherein the compound is: 2-bromo-6-chloro-N,N-dimethyl-1-phenol-4-sulfonamide.

7. A method according to claim 1 wherein the compound is: 2,6-dichloro-N,N-dimethyl-1-phenol-4-sulfonamide.

8. A method according to claim 1 wherein the compound is: 2,6-dibromo-4-(dimethylsulfamoyl)phenyl carbamic acid methyl ester.

* * * * *